United States Patent
Ryo et al.

(10) Patent No.: US 9,689,798 B1
(45) Date of Patent: Jun. 27, 2017

(54) PROTECTIVE FILM DETECTING METHOD FOR LASER PROCESSING

(71) Applicant: DISCO CORPORATION, Tokyo (JP)

(72) Inventors: Senichi Ryo, Tokyo (JP); Yukinobu Ohura, Tokyo (JP)

(73) Assignee: Disco Corporation, Tokyo (JP)

( * ) Notice: Subject to any disclaimer, the term of this patent is extended or adjusted under 35 U.S.C. 154(b) by 0 days.

(21) Appl. No.: 15/373,735

(22) Filed: Dec. 9, 2016

(30) Foreign Application Priority Data

Dec. 18, 2015 (JP) .................................. 2015-247143

(51) Int. Cl.
| | |
|---|---|
| *F21V 9/16* | (2006.01) |
| *G01N 21/64* | (2006.01) |
| *G03F 7/20* | (2006.01) |
| *H01L 21/66* | (2006.01) |
| *C23C 16/52* | (2006.01) |

(52) U.S. Cl.
CPC ............ *G01N 21/64* (2013.01); *C23C 16/52* (2013.01); *G01N 2021/6495* (2013.01); *G03F 7/70608* (2013.01); *H01L 22/12* (2013.01); *H01L 22/26* (2013.01)

(58) Field of Classification Search
CPC ... H01L 22/26; H01L 22/12; H01L 21/67253; G03F 7/70608; C23C 16/52
See application file for complete search history.

(56) References Cited

U.S. PATENT DOCUMENTS

| | | | | |
|---|---|---|---|---|
| 4,841,156 A | * | 6/1989 | May ................... | G01B 11/0658 250/459.1 |
| 2002/0127950 A1 | * | 9/2002 | Hirose ................. | B24B 37/013 451/6 |
| 2003/0118148 A1 | * | 6/2003 | Kataoka ................. | G01J 3/443 378/44 |
| 2003/0193672 A1 | * | 10/2003 | Okada ................ | G01B 11/0658 356/630 |
| 2005/0244570 A1 | * | 11/2005 | Tanase .................... | C23C 14/12 427/10 |
| 2008/0078948 A1 | * | 4/2008 | Saito ....................... | H01L 22/26 250/492.2 |

FOREIGN PATENT DOCUMENTS

| | | |
|---|---|---|
| JP | 06-120334 | 4/1994 |
| JP | 2004-322168 | 11/2004 |

* cited by examiner

*Primary Examiner* — David J Makiya
*Assistant Examiner* — Kenneth J Malkowski
(74) *Attorney, Agent, or Firm* — Greer Burns & Crain Ltd.

(57) ABSTRACT

Disclosed herein is a protective film detecting method of detecting the formed condition of a protective film formed on the front side of a workpiece. The protective film detecting method includes a fluorescence intensity measuring step of forming a plurality of reference protective films having different thicknesses on the front sides of a plurality of reference workpieces, next applying excitation light absorbable by an absorbing agent contained in each reference protective film to each reference protective film, and next measuring the intensity of fluorescence emitted from the absorbing agent due to the absorption of the excitation light, and a threshold deciding step of deciding a threshold of the fluorescence intensity corresponding to a desired one of the different thicknesses of the reference protective films according to the fluorescence intensity measured above.

3 Claims, 10 Drawing Sheets

PROTECTIVE FILM DETECTING METHOD FOR LASER PROCESSING

BACKGROUND OF THE INVENTION

Field of the Invention

The present invention relates to a method of determining whether or not a protective film has a desired thickness, the protective film being formed on the front side of a workpiece such as a semiconductor wafer in dividing the workpiece by laser processing.

Description of the Related Art

As a method of dividing a workpiece such as a semiconductor wafer along streets (division lines), there is a method of laser-processing the workpiece along the streets to thereby divide the workpiece (see Japanese Patent Laid-open No. 1994-120334, for example). In the laser processing method described in Japanese Patent Laid-open No. 1994-120334, a laser beam is applied to the semiconductor wafer along the streets to generate thermal energy on the semiconductor wafer in an area corresponding to the streets, thereby continuously processing the semiconductor wafer in this area irradiated with the laser beam. There is a case that the thermal energy may be concentrated in this laser irradiated area on the semiconductor wafer to cause the generation of debris (processing dust). Accordingly, there is a problem such that this debris may adhere to bonding pads or the like on large scale integrations (LSIs) formed on the semiconductor wafer, causing a reduction in quality of semiconductor chips.

To solve this problem, the present applicant has proposed a laser processing method including the steps of forming a water-soluble protective film on the front side of a semiconductor wafer and next applying a laser beam through this protective film to the semiconductor wafer (see Japanese Patent Laid-open No. 2004-322168, for example). In the laser processing method described in Japanese Patent Laid-open No. 2004-322168, the semiconductor wafer is processed through the protective film, so that the debris scattered in laser processing can be made to adhere to the protective film. Thereafter, in a cleaning step, the protective film is removed together with the debris. Accordingly, the adhesion of the debris to the front side of the semiconductor wafer can be suppressed to prevent a reduction in quality of the semiconductor chips.

SUMMARY OF THE INVENTION

However, in processing the semiconductor wafer through the protective film by using a laser beam, it is preferable to set the thickness of the protective film evenly to a predetermined value. That is, the thickness of the protective film has an effect on the result of laser processing. If the thickness of the protective film is less than the predetermined value, there is a possibility that the wafer cannot be sufficiently protected from the debris, whereas if the thickness of the protective film is greater than the predetermined value, there is a possibility that laser processing may be hindered by the protective film. It is therefore desired to accurately measure the thickness of the protective film formed on the semiconductor wafer before laser processing. Further, if much time is required for the measurement of the thickness of the protective film, the productivity in laser processing is reduced.

It is therefore an object of the present invention to provide a protective film detecting method which can accurately and simply detect the formed condition of a protective film formed on the front side of a workpiece.

In accordance with an aspect of the present invention, there is provided a protective film detecting method of detecting the formed condition of a protective film formed on the front side of a workpiece, so as to protect the front side of the workpiece from processing dust generated in laser-processing the workpiece by applying a pulsed laser beam having a wavelength in an ultraviolet region or visible region to the workpiece, the protective film being formed of a water-soluble resin containing an absorbing agent capable of absorbing the pulsed laser beam, the protective film detecting method including a fluorescence intensity measuring step of forming a plurality of reference protective films having different thicknesses on the front sides of a plurality of reference workpieces, next applying excitation light absorbable by the absorbing agent to the reference protective films, and next measuring the intensity of fluorescence emitted from the absorbing agent contained in each reference protective film due to the absorption of the excitation light; a threshold deciding step of deciding a threshold of the fluorescence intensity corresponding to a desired one of the different thicknesses of the reference protective films according to the fluorescence intensity measured in the fluorescence intensity measuring step; and a determining step of applying the excitation light to the protective film formed on the front side of the workpiece, next measuring the intensity of fluorescence emitted from the absorbing agent contained in the protective film due to the absorption of the excitation light, next comparing the fluorescence intensity from the absorbing agent contained in the protective film with the threshold decided in the threshold deciding step, and next determining whether or not the protective film has the desired thickness.

Preferably, the wavelength of the pulsed laser beam is 355 nm; the wavelength of the excitation light is in the range of 350 to 400 nm; and the peak wavelength of the fluorescence at which the fluorescence intensity becomes a peak value is longer than the wavelength of the excitation light and falls within the range of 365 to 600 nm. Alternatively, the wavelength of the pulsed laser beam is 532 nm; the wavelength of the excitation light is in the range of 480 to 600 nm; and the peak wavelength of the fluorescence at which the fluorescence intensity becomes a peak value is longer than the wavelength of the excitation light and falls within the range of 570 to 700 nm.

According to the present invention, the protective film is formed of a water-soluble resin containing an absorbing agent. This protective film is formed on the front side of the workpiece, and the excitation light is applied to the protective film. At this time, the absorbing agent contained in the protective film absorbs the excitation light to emit fluorescence. Then, the intensity of this fluorescence is measured and it is determined whether or not the protective film has a desired thickness according to the fluorescence intensity measured above. Accordingly, the thickness of the protective film can be measured accurately and easily by using the excitation light having an absorption wavelength to the absorbing agent contained in the protective film. Further, as the excitation light for the detection of the protective film, continuous-wave light having a single wavelength is used. Accordingly, damage to the protective film due to the excitation light can be suppressed and it can be accurately determined whether or not the protective film has a desired thickness.

The above and other objects, features and advantages of the present invention and the manner of realizing them will become more apparent, and the invention itself will best be understood from a study of the following description and appended claims with reference to the attached drawings showing a preferred embodiment of the invention.

DETAILED DESCRIPTION OF THE PREFERRED EMBODIMENT

Figure 1:
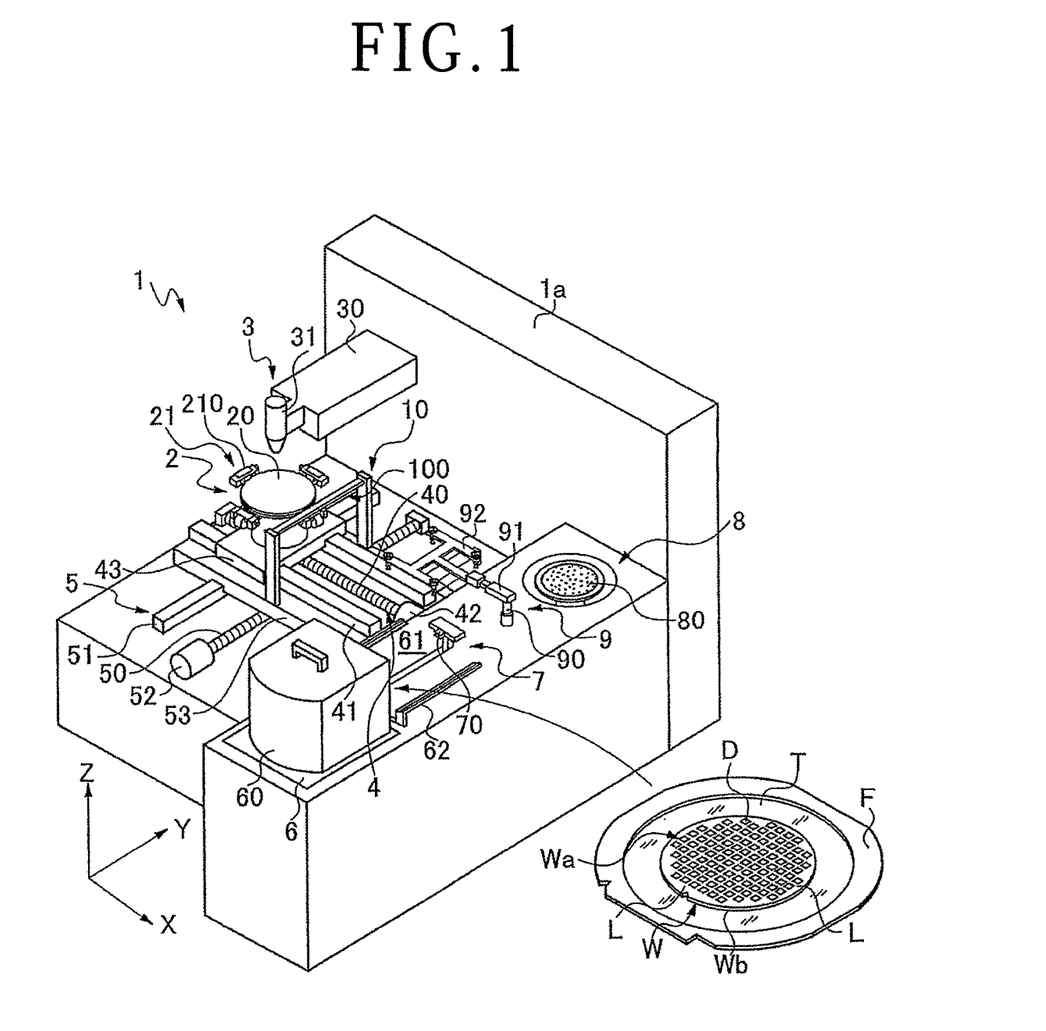
FIG. 1 is a perspective view of a laser processing apparatus for use in performing the present invention.

Referring to FIG. 1, there is shown a laser processing apparatus 1 for use in performing the present invention. The laser processing apparatus 1 shown in FIG. 1 has a function of forming a protective film on the front side Wa of a workpiece W, a function of determining whether or not the protective film formed has a desired thickness, and a function of laser-processing the workpiece W. The laser processing apparatus 1 includes a cassette mounting area 6 for mounting a cassette 60 storing the workpiece W as a target to be laser-processed, workpiece handling means 7 for handling the workpiece W to take it out of the cassette 60 before laser processing or store it into the cassette 60 after laser processing, protective film forming means 8 for forming a protective film on the front side Wa of the workpiece W taken out of the cassette 60, a chuck table 2 for holding the workpiece W on which the protective film has been formed, and laser beam applying means 3 for applying a laser beam to the workpiece W held on the chuck table 2.

The cassette mounting area 6 is vertically movable. A plurality of slots for receiving a plurality workpieces W are formed in the cassette 60 so as to be vertically arranged at different levels. By vertically moving the cassette mounting area 6, a desired one of the slots can be positioned at a predetermined height in taking the workpiece W out of the cassette 60 or storing it into the cassette 60. A plurality of crossing division lines L are formed on the front side Wa of the workpiece W stored in the cassette 60 to thereby partition the front side Wa into a plurality of separate regions where a plurality of devices D are formed. The back side Wb of the workpiece W is attached to a tape T supported at its peripheral portion to a frame F. Accordingly, the workpiece W stored in the cassette 60 is supported through the tape T to the frame F in the condition where the front side Wa of the workpiece W is exposed.

The workpiece handling means 7 is movable in the longitudinal direction (Y direction) of the apparatus 1. The workpiece handling means 7 includes a holding (pinching) portion 70 for holding the frame F supporting the workpiece W. In the condition where the frame F is held by the holding portion 70, the workpiece W supported to the frame F can be taken out of the cassette 60 by operating the workpiece handling means 7. Conversely, when the frame F is pushed by the workpiece handling means 7 in the Y direction toward the front side of the apparatus 1, the workpiece W can be stored into a desired slot in the cassette 60. A temporary setting area 61 for temporarily setting the workpiece W after taking it out of the cassette 60 or before storing it into the cassette 60 is defined on the rear side of the cassette mounting area 6 in the Y direction. The temporary setting area 61 is provided with a guide portion 62 for guiding the frame F and setting the workpiece W at a predetermined position.

Figure 2:
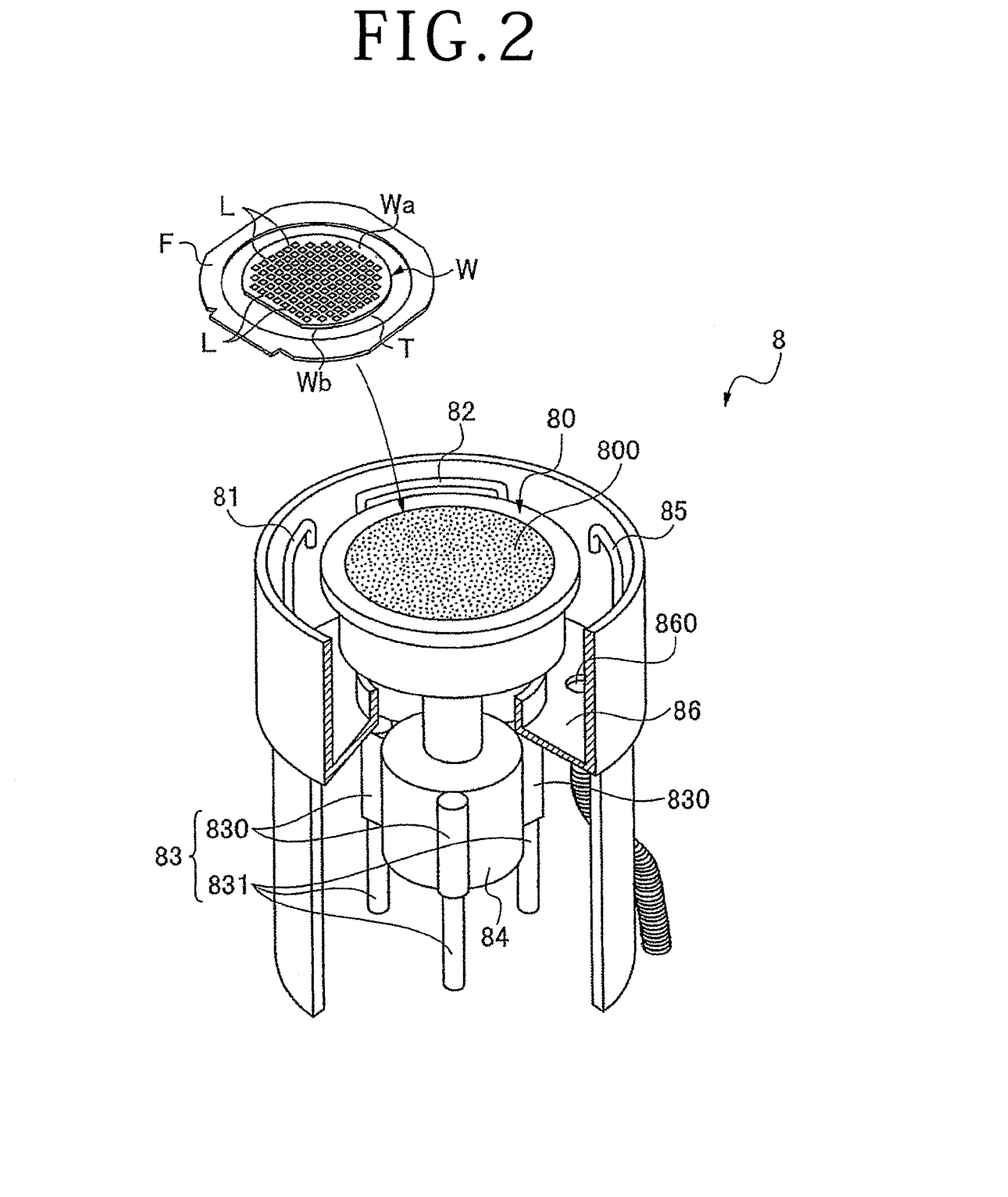
FIG. 2 is a perspective view of protective film forming means included in the laser processing apparatus shown in FIG. 1.

As shown in FIG. 2, the protective film forming means 8 includes a rotatable holding table 80 for holding the workpiece W supported to the frame F under suction, a water-soluble liquid resin nozzle 81 for dispensing a water-soluble liquid resin to the workpiece W held on the holding table 80, a cleaning liquid nozzle 82 for discharging a cleaning liquid to the workpiece W, and an air nozzle 85 for discharging air under high pressure. The holding table 80 includes a porous holding member 800 connected to a vacuum source (not shown). The holding table 80 is vertically movable by an elevating portion 83 and rotatable by a motor 84. A receptacle portion 88 for receiving the water-soluble liquid resin or the cleaning liquid is provided below the holding table 80 so as to surround the holding table 80. The bottom of the receptacle portion 88 is formed with a drain opening 880 for draining the water-soluble liquid resin or the cleaning liquid.

The elevating portion 83 is composed of a plurality of air cylinders 830 fixed to the side surface (cylindrical outer surface) of the motor 84 and a plurality of rods 831 corresponding to the plural air cylinders 830. When the air cylinders 830 are operated, the motor 84 and the holding table 80 can be vertically moved together.

As shown in FIG. 1, a transfer mechanism 9 is provided between the temporary setting area 61 and the protective film forming means 8. The transfer mechanism 9 includes a rotating shaft 90 having an axis extending in a vertical direction (Z direction), an expansion arm 91 horizontally extending from the upper end of the rotating shaft 90, and a suction holding portion 92 provided at the front end of the expansion arm 91 for holding the frame F under suction. The suction holding portion 92 can be adjusted in position in an X-Y plane by the rotation of the rotating shaft 90 and the expansion/contraction of the expansion arm 91. The suction holding portion 92 can also be adjusted in position in the vertical direction (Z direction) by the vertical movement of the rotating shaft 90.

The chuck table 2 includes a suction holding portion 20 for holding the workpiece W under suction. A fixing portion 21 for fixing the frame F supporting the workpiece W is provided around the suction holding portion 20. The fixing portion 21 includes a pressing portion 210 for pressing the frame F from the upper side thereof.

The chuck table 2 is supported by feeding means 4 so as to be movable in a feeding direction (X direction) and also supported by indexing means 5 so as to be movable in an indexing direction (Y direction).

The feeding means 4 is composed of a ball screw 40 having an axis extending in the X direction, a pair of guide rails 41 parallel to the ball screw 40, a motor 42 connected to one end of the ball screw 40, and a slide portion 43 having an internal nut (not shown) threadedly engaged with the ball screw 40 and having a lower portion slidably engaged with the guide rails 41. Accordingly, when the ball screw 40 is rotated by the motor 42, the slide portion 43 is slidingly moved on the guide rails 41 in the X direction to thereby move the chuck table 2 in the X direction.

The chuck table 2 and the feeding means 4 are supported by the indexing means 5 so as to be movable in the Y direction. The indexing means 5 is composed of a ball screw 50 having an axis extending in the Y direction, a pair of guide rails 51 parallel to the ball screw 50, a motor 52 connected to one end of the ball screw 50, and a platelike base 53 having an internal nut (not shown) threadedly engaged with the ball screw 50 and having a lower portion slidably engaged with the guide rails 51. Accordingly, when the ball screw 50 is rotated by the motor 52, the base 53 is slidingly moved on the guide rails 51 in the Y direction to thereby move the chuck table 2 and the feeding means 4 in the Y direction.

The laser beam applying means 3 includes a base 30 fixed to a rear wall 1a of the apparatus 1 and a laser head 31 fixed to the front end of the base 30. The laser head 31 functions to radiate a laser beam along an optical path extending in the Z direction.

While the feeding means 4 and the indexing means 5 are so configured as to move the chuck table 2 in the X direction and the Y direction, respectively, and the laser beam applying means 3 is not moved in the laser processing apparatus 1 shown in FIG. 1, the configuration is not limited to that shown in FIG. 1, provided that the chuck table 2 and the laser beam applying means 3 are relatively moved in the X direction and in the Y direction. For example, the chuck table 2 may be moved in the X direction and the laser beam applying means 3 may be moved in the Y direction. As another configuration, the chuck table 2 may not be moved and the laser beam applying means 3 may be moved both in the X direction and in the Y direction.

Figure 3A:
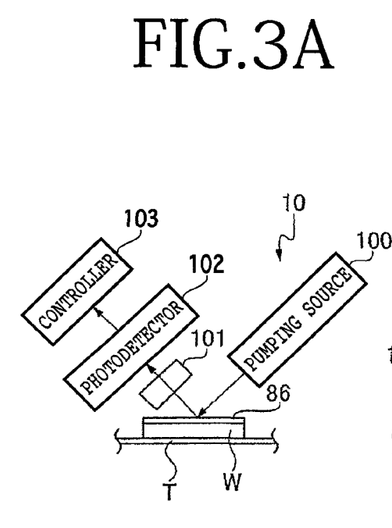
FIG. 3A is a schematic view showing the configuration of a protective film detecting unit included in the laser processing apparatus shown in FIG. 1 in the case of detecting fluorescence at a certain position on the front side of a workpiece W.

The laser processing apparatus 1 further includes a protective film detecting unit 10 for applying light to the protective film formed on the workpiece W by the protective film forming means 8 and detecting fluorescence emitted from the protective film to thereby detect whether or not the protective film formed on the workpiece W has a desired thickness. The protective film detecting unit 10 may be provided in the same space as that of the protective film forming means 8 or in the same space as that of the laser beam applying means 3 as in this preferred embodiment. Alternatively, the protective film detecting unit 10 may be provided independently of the laser processing apparatus 1. As shown in FIG. 3A, the protective film detecting unit 10 includes a pumping source 100, an optical filter 101 for preventing that light emitted from the pumping source 100 may enter a photodetector 102, the photodetector 102 for detecting fluorescence emitted from a protective film 86 formed on the workpiece W, and a controller 103 for receiving information from the photodetector 102 and performing processing according to the information received.

Figure 3B:
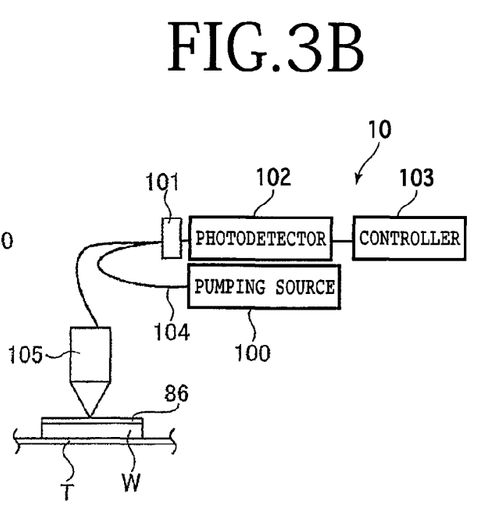
FIG. 3B is a schematic view similar to FIG. 3A, showing the case that a fiber is used.

As the pumping source 100 for use in detecting fluorescence at a certain position on the workpiece W as shown in FIG. 3A, a light-emitting diode (LED) or a continuous-wave (CW) laser may be used, for example. Further, as a method of detecting fluorescence at a certain position on the workpiece W, a method (configuration) shown in FIG. 3B may be used. The configuration shown in FIG. 3B includes a pumping source 100, a fiber 104 for guiding light emitted from the pumping source 100 to a protective film 86 present on the workpiece W, a probe 105 for convergently applying the light guided by the fiber 104 to the protective film 86 and guiding reflected light and fluorescence from the protective film 86 to an optical filter 101, the optical filter 101 for blocking only the reflected light from the probe 105, a photodetector 102 for detecting only the fluorescence from the protective film 86, and a controller 103 for receiving information from the photodetector 102 and performing processing according to the information received.

Figure 3C:
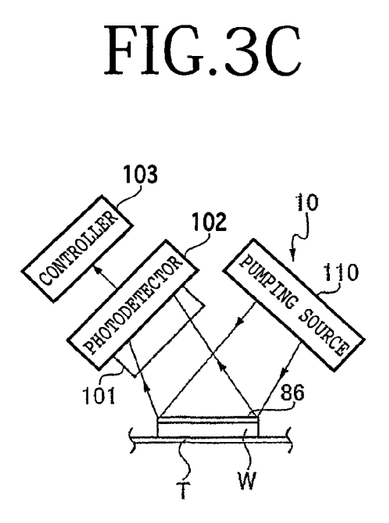
FIG. 3C is a schematic view showing the configuration of the protective film detecting unit in the case of detecting fluorescence on a large area of the front side of the workpiece W.

As a method of detecting fluorescence on a large area or the whole surface of the front side of the workpiece W, a method (configuration) shown in FIG. 3C may be used. The configuration shown in FIG. 3C includes a pumping source 110, an optical filter 101 for preventing that light emitted from the pumping source 110 may enter a photodetector 102, the photodetector 102 for detecting fluorescence from a protective film 86 formed on the workpiece W, and a controller 103 for receiving information from the photodetector 102 and performing processing according to the information received. As the pumping source 110, an LED array is preferably used.

Figure 3D:
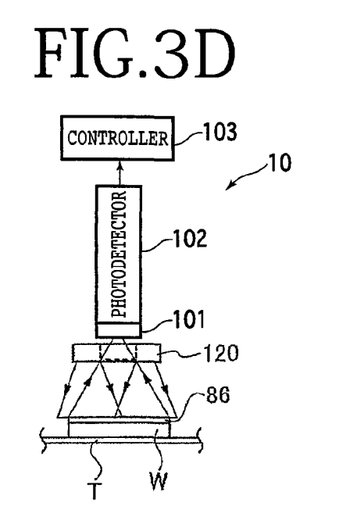
FIG. 3D is a schematic view similar to FIG. 3C, showing the case that a doughnut-shaped pumping source is used.

As another method of detecting fluorescence on a large area or the whole surface of the front side of the workpiece W, a method (configuration) shown in FIG. 3D may be used. The configuration shown in FIG. 3D includes a pumping source 120, an optical filter 101 for preventing that light emitted from the pumping source 120 may enter a photodetector 102, the photodetector 102 for detecting fluorescence from a protective film 86 formed on the workpiece W, and a controller 103 for receiving information from the photodetector 102 and performing processing according to the information received. As the pumping source 120, an LED array having a central hole (e.g., a doughnut-shaped LED array) is preferably used.

In performing laser processing to the workpiece W by using the laser processing apparatus 1 shown in FIG. 1, a protective film is preliminarily formed on the front side Wa of the workpiece W and it is determined whether or not this protective film has a desired thickness before laser processing according to the following method. When the protective film has a desired thickness, the workpiece W is laser-processed.

(1) Preparation Step

Prior to inspecting the thickness of a protective film to be actually formed on the front side Wa of the workpiece W to be laser-processed, data as a criterion for determination is obtained in advance.

(1a) Reference Spectrum Making Step

A plurality of workpieces W are prepared. A tape T is attached to the back side Wb of each workpiece W, and a ring frame F is attached to the peripheral portion of the tape T. In this manner, each workpiece W is supported through the tape T to the frame F so as to form a unit. These plural workpieces W supported to the frames F are stored in the cassette 60. Each workpiece W stored in the cassette 60 is taken out by the workpiece handling means 7 in such a manner that the frame F is held by the holding portion 70 of the workpiece handling means 7. The workpiece W is then carried to the temporary setting area 61 by the workpiece handling means 7. After setting the workpiece W at a predetermined position in the temporary setting area 61, the workpiece W is transferred to the protective film forming means 8 by operating the transfer mechanism 9. In the protective film forming means 8, the workpiece W is held through the tape T on the holding table 80 in the condition where the front side Wa of the workpiece W is exposed upward.

Figure 4A:
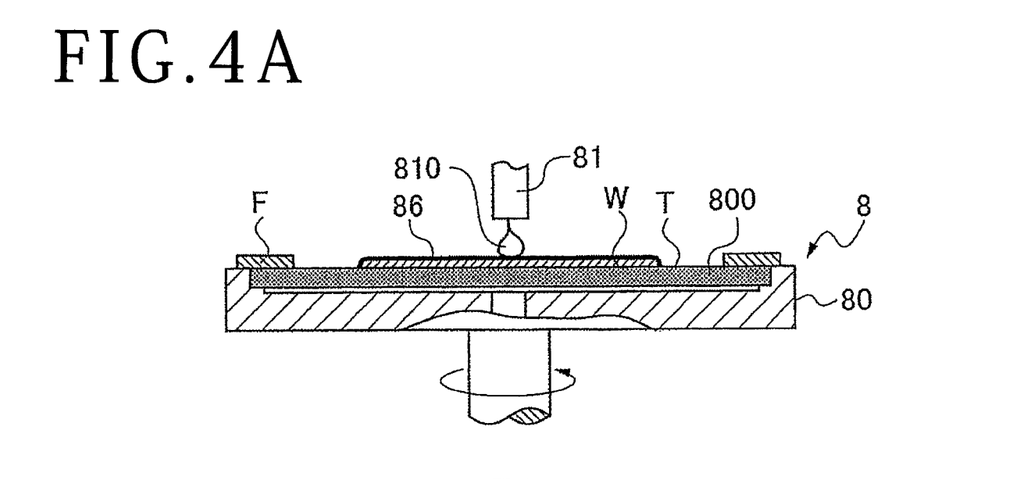
FIG. 4A is a sectional view showing a condition where a water-soluble liquid resin is applied to the front side of a wafer to form a protective film.

As shown in FIG. 4A, the holding table 80 is next rotated and a water-soluble liquid resin 810 is dropped from the liquid resin nozzle 81 onto the front side Wa of the workpiece W at the center thereof. The water-soluble liquid resin 810 is a material for forming a protective film. This material is not especially limited, provided that it is soluble in water or the like and can be formed into a film after coating and drying. Examples of the water-soluble liquid resin 810 include polyvinyl alcohol, polyvinyl pyrrolidone, polyethylene glycol having 5 or more repetition units of oxyethylene, polyethylene oxide, methyl cellulose, ethyl cellulose, hydroxypropyl cellulose, polyacrylic acid, block copolymer of polyvinyl alcohol and polyacrylic acid, block copolymer of polyvinyl alcohol and polyacrylate, and polyglycerol. These materials may be used solely or in combination.

The water-soluble liquid resin 810 contains an absorbing agent for absorbing light having a wavelength equal to the wavelength of a laser beam to be applied from the laser beam applying means 3. The absorbing agent is contained in an amount of about 0.01 to 10 parts by weight per 100 parts by weight of water-soluble resin. For example, in the case of using a laser beam having an ultraviolet region (e.g., a wavelength of 355 nm) in a laser processing step to be hereinafter described, an ultraviolet absorbing agent for absorbing light having a wavelength in the ultraviolet region (e.g., in the wavelength range of 250 to 400 nm) is used as the absorbing agent to be added to the water-soluble liquid resin 810. Examples of this ultraviolet absorbing agent include a plastic additive such as benzophenone series, benzotriazole series, triazine series, and benzoate series. In the case of using a laser beam having a visible region (e.g., a wavelength of 532 nm), a visible light absorbing agent for absorbing light in the visible region (e.g., in the wavelength range of 480 to 600 nm) is used as the absorbing agent to be added to the water-soluble liquid resin 810. Examples of this visible light absorbing agent include a coloring matter such as phthalocyanine series, quinacridone series, pigment red series, pigment blue series, and malachite green series.

Figure 4B:
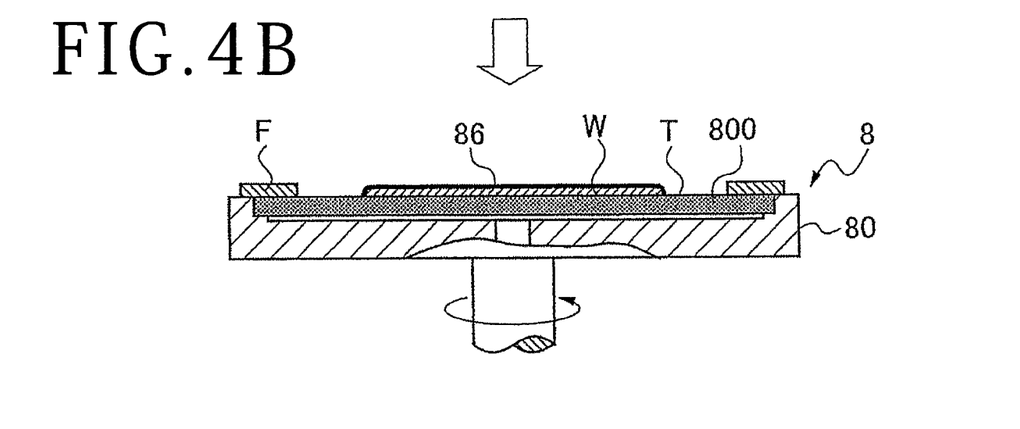
FIG. 4B is a sectional view showing a condition where the protective film formed on the front side of the wafer is dried.

When the holding table 80 is rotated, the water-soluble liquid resin 810 dropped onto the front side Wa of the workpiece W at the center thereof is radially spread on the whole surface of the front side Wa by a centrifugal force. At the time the water-soluble liquid resin 810 is applied by a predetermined amount, the supply of the water-soluble liquid resin 810 from the liquid resin nozzle 81 is stopped. After applying the predetermined amount of water-soluble liquid resin 810 to the front side Wa of the workpiece W as mentioned above, the water-soluble liquid resin 810 is dried by the rotation of the holding table 80 as shown in FIG. 4B, thereby solidifying the water-soluble liquid resin 810 to form a protective film 86 on the front side Wa of the workpiece W.

The water-soluble liquid resin 810 may be dried by applying light from a lamp (e.g., infrared lamp, halogen lamp, tungsten lamp, or mercury lamp), LED, pulsed laser, or xenone pulse lamp. In this case, pulse light from a pulsed laser or xenone pulse lamp is preferably applied, so as to avoid a rise in temperature of the protective film 86. In the case that the temperature rise is small, the light may be applied at a time. In the case that the temperature rise is large, the light is applied plural times. In the case of applying the light plural times, the protective film 86 may be allowed to stand until the temperature is naturally decreased or may be cooled by air. Further, the water-soluble liquid resin 810 applied to the workpiece W may be subjected to baking by using a hot plate. Further, the water-soluble liquid resin 810 may be applied by a spin coating method as in this preferred embodiment or by a spray coating method. Further, the water-soluble liquid resin 810 may be discharged from a slit-shaped nozzle. In the case that a surface active agent is contained in the water-soluble liquid resin 810, it is unnecessary to dry the water-soluble liquid resin 810 applied to the workpiece W. By using such a drying method, a protective film having a thickness of 2 µm or more can be dried in a short time. In such a case of large film thickness, it is difficult to dry the protective film by using a centrifugal force. By increasing the thickness of the protective film, fluorescence intensity can be increased and it can be accurately determined whether or not the protective film has a desired thickness. Further, by increasing the thickness of the protective film on a wafer with bumps, the protective film can be easily formed on a highest part of each bump. In general, when a wafer as a workpiece is laser-processed, a plasma is generated from the material of the wafer to break a thin part of the protective film, so that there is a possibility that a residue may be deposited on the front side of the wafer. This residue is not water-soluble and it is therefore difficult to remove this residue together with the protective film after performing laser processing. Accordingly, it is necessary to form a protective film having a thickness capable of resisting the breakage by the laser processing and the plasma generated thereby.

Further, in the case that the protective film is deposited to the frame F, it may be dried by using the lamp mentioned above or may be removed from the frame F by discharging water to only the frame F.

In this manner, the protective film 86 is formed on the front side Wa of each workpiece W, wherein the plural protective films 86 formed in this step have different thicknesses. The thickness of each protective film 86 may be changed according to the rotational speed of the holding table 80 and the duration of rotation thereof in performing the spin coating. For example, five kinds of workpieces W with the protective films 86 having different thicknesses of 1.2 μm, 2.3 μm, 2.7 μm, 3.1 μm, and 5.0 μm are prepared. Alternatively, a plurality of protective films having different thicknesses may be formed at plural portions on one workpiece rather than preparing a plurality of workpieces with plural protective films having different thicknesses.

After preparing the plural workpieces W with the protective films 86 having different thicknesses, a fluorescence spectrum is made for each of the plural workpieces W with the protective films 86 having different thicknesses, by using the protective film detecting unit 10.

Referring back to FIG. 1, each workpiece W having the protective film 86 is transferred to the chuck table 2 by operating the transfer mechanism 9. The workpiece W is held through the tape T on the suction holding portion 20 of the chuck table 2. Thereafter, the chuck table 2 is moved in the −X direction (to the left side as viewed in FIG. 1) until reaching a position directly below the protective film detecting unit 10.

When the chuck table 2 is positioned directly below the protective film detecting unit 10, the light emitted from the pumping source 100 shown in FIG. 3A, for example, is applied to the protective film 86. The light emitted from the pumping source 100 is ultraviolet light or visible light, which is continuous-wave light having a single wavelength. The light having a single wavelength means light having a limited wavelength component. That is, this light may have a certain wavelength range. For example, in the case that the absorbing agent contained in the protective film has absorptivity to ultraviolet light, the light (excitation light) to be emitted from the pumping source 100 is ultraviolet light. For example, in the case that the wavelength of a pulsed laser beam to be used in laser processing of the workpiece W is 355 nm, light having a longer wavelength (e.g., 355 to 410 nm) is preferably used as the excitation light. For example, ultraviolet light having a peak wavelength of 365±10 nm or a peak wavelength of 385±10 nm may be used. Although light having a wavelength less than or equal to 355 nm may be used, there is a technical problem such that high power cannot be obtained or the protective film may be modified. The power of this ultraviolet light is set to 10 to 100 mW/cm$^2$, for example.

In the case that the wavelength of the pulsed laser beam to be used in laser processing of the workpiece W is 532 nm, light having a wavelength of 480 to 600 nm, for example, is preferably used as the excitation light. For example, visible light having a peak wavelength of 532±10 nm or a peak wavelength of 570±10 nm may be used. In the case of excitation by visible light, the wavelength of the visible light is not especially limited, but the wavelength may be changed according to the absorbing agent to be added to the protective film. The power of this visible light is set to 10 to 100 mW/cm$^2$, for example. The continuous-wave light having a single wavelength is used for the following reason. The reason why continuous-wave light is used is to suppress the modification of the protective film. Further, the reason why light having a single wavelength is used is to accurately determine whether or not the protective film has a desired thickness. That is, if any light other than fluorescence enters a photodetector in measuring the fluorescence emitted from the protective film, it is impossible to distinguish the fluorescence from the other light. The continuous-wave light may be provided by a lamp such as a halogen lamp, tungsten lamp, and mercury lamp, a CW laser, or an LED. In the case of using a lamp such as a halogen lamp, tungsten lamp, and mercury lamp, the light having a single wavelength can be obtained by using an optical component such as a filter. The light emitted from an LED slightly contains a wavelength component other than a peak wavelength. Accordingly, in the case of using an LED, the wavelength component other than the peak wavelength may be removed by using an optical component. From the viewpoint of applying the light to a large area with high intensity, an LED is preferably used to generate the continuous-wave light having a single wavelength.

Figure 5:
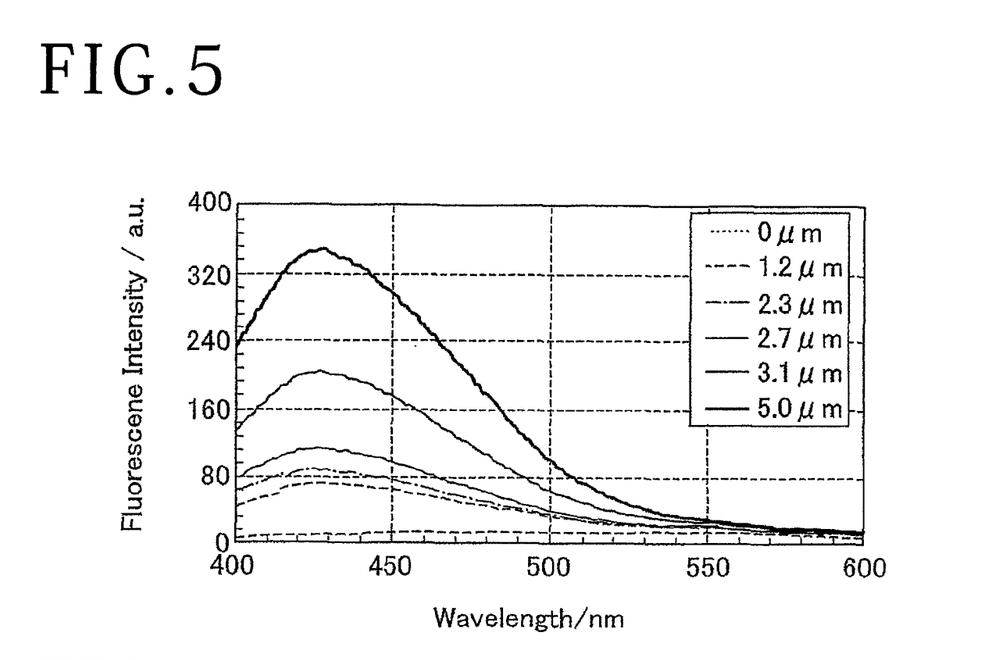
FIG. 5 is a graph showing a fluorescence spectrum in the case that light having a wavelength of 365 nm is applied to a pattern wafer.

When the light applied to the protective film 86 is absorbed by the absorbing agent, the molecules of the absorbing agent in a ground state are excited and the energy of the molecules therefore becomes a high unstable state. Thereafter, the state of the molecules is dropped to a relaxation caused electronic singlet state. Thereafter, the molecules of the absorbing agent emit light having a wavelength longer than that of the light emitted from the pumping source 100 and dissipate energy to restore the ground state. This light emitted from the molecules of the absorbing agent in restoring the ground state is fluorescence. The fluorescence emitted from the protective film 86 is detected by the photodetector 102. To detect only the fluorescence, the reflected light from the protective film 86 is blocked by the optical filter 101 located before the photodetector 102. The intensity of the fluorescence detected by the photodetector 102 is measured by the controller 103. In the controller 103, a fluorescence spectrum showing the relation between the wavelength of the fluorescence and the intensity of the fluorescence is made as shown in FIG. 5 or a value for the fluorescence intensity at a certain wavelength can be recognized. Such a fluorescence spectrum or fluorescence intensity is made for each of the plural workpieces W with the protective films 86 having different thicknesses. The fluorescence intensity may be measured on the whole surface of each workpiece W or at only a predetermined position on each workpiece W. In the fluorescence spectrum, the fluorescence intensity (along the vertical axis of the graph shown in FIG. 5) increases with an increase in thickness of the protective film 86.

The fluorescence spectrum as a reference is made according to the kind of the workpiece W. For example, a fluorescence spectrum for an ordinary pattern wafer with no bumps formed on the front side (FIG. 5) and a fluorescence spectrum for a bump wafer with bumps formed on the front side (FIG. 6) are made because the peak intensity is different. Accordingly, the fluorescence spectrum for the pattern wafer and the fluorescence spectrum for the bump wafer are made for the protective films 86 having different thicknesses and then stored into the controller 103 in advance.

Figure 6:
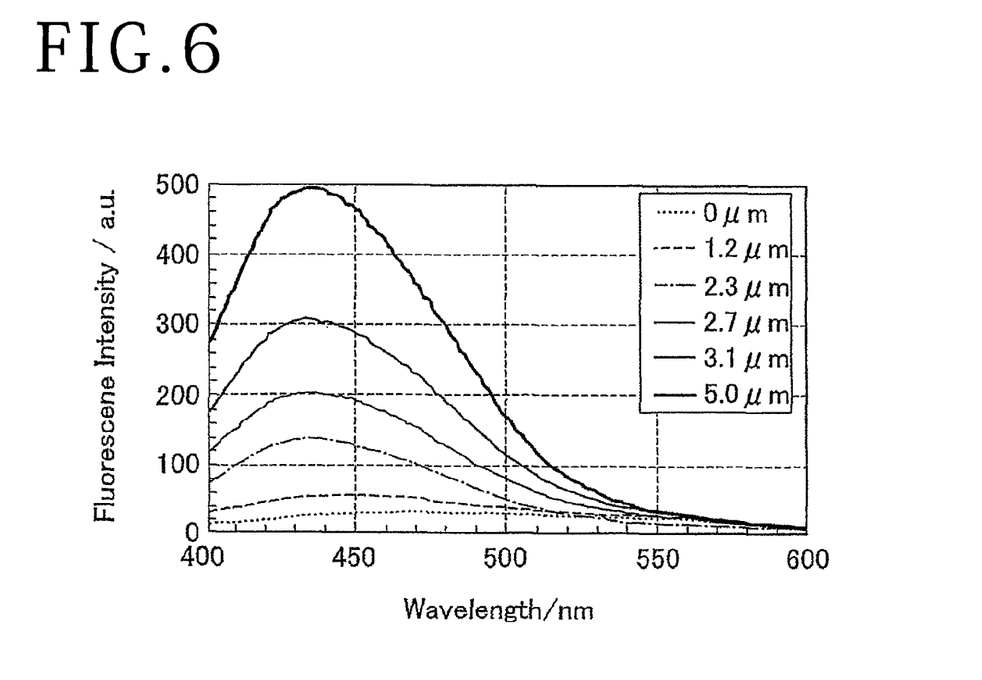
FIG. 6 is a graph showing a fluorescence spectrum in the case that light having a wavelength of 365 nm is applied to a bump wafer.
Figure 7:
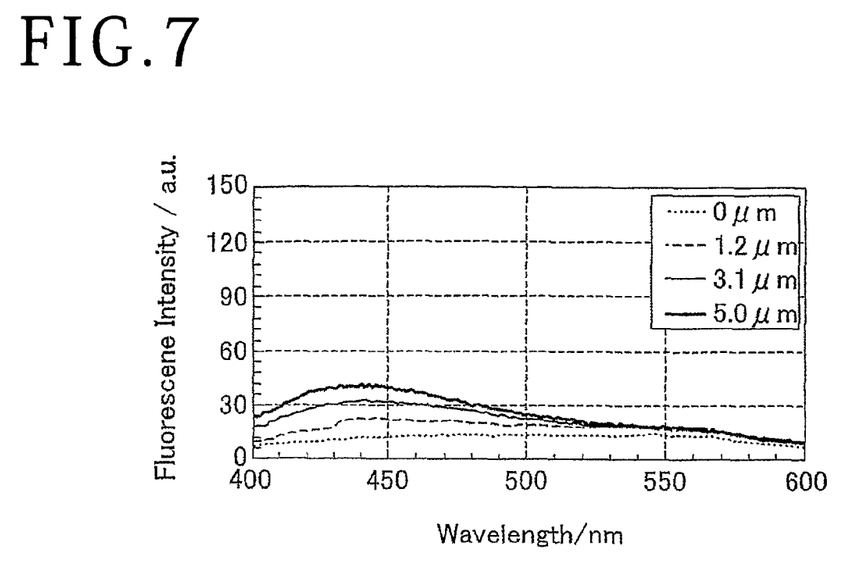
FIG. 7 is a graph showing a fluorescence spectrum in the case that light having a wavelength of 385 nm is applied to a pattern wafer.
Figure 8:
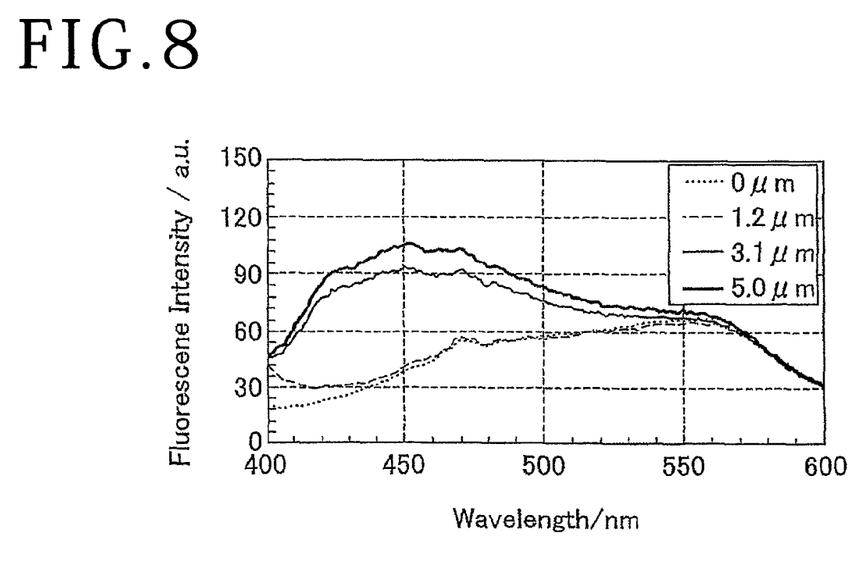
FIG. 8 is a graph showing a fluorescence spectrum in the case that light having a wavelength of 385 nm is applied to a bump wafer.
Figure 9:
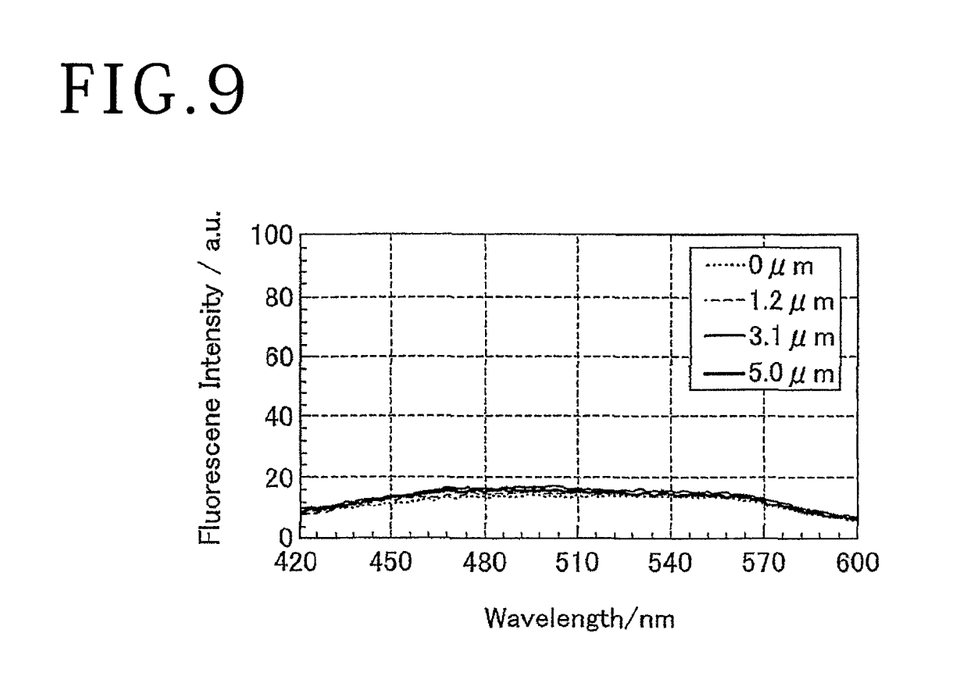
FIG. 9 is a graph showing a fluorescence spectrum in the case that light having a wavelength of 405 nm is applied to a pattern wafer.
Figure 10:
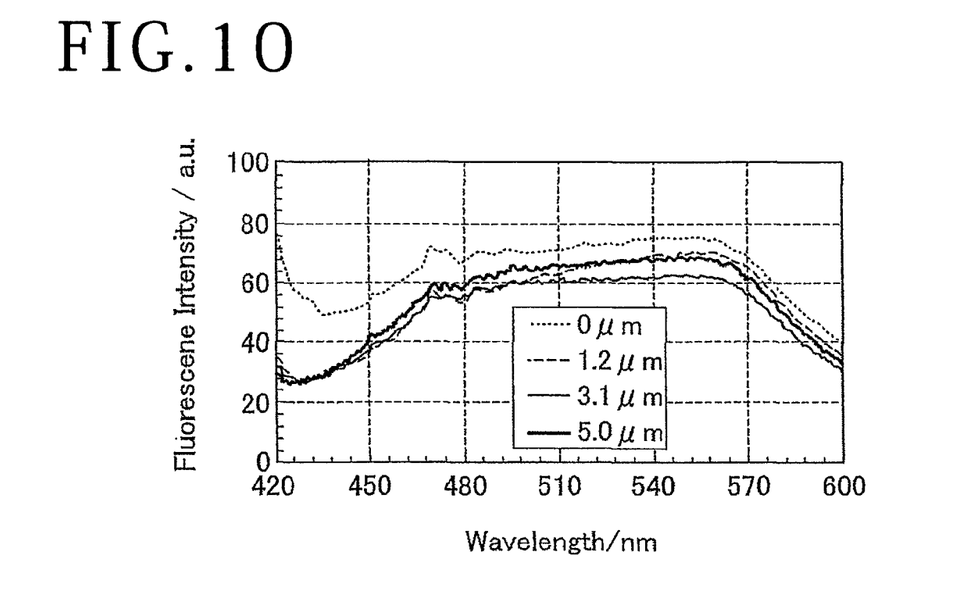
FIG. 10 is a graph showing a fluorescence spectrum in the case that light having a wavelength of 405 nm is applied to a bump wafer.

Each of the fluorescence spectra shown in FIGS. 5 and 6 shows the dependence of the fluorescence intensity upon the thickness of the protective film 86 in the case that the wavelength of the light to be applied to the protective film 86 is set to 365 nm. Also in the case that the wavelength of the light to be applied to the protective film 86 is different, the fluorescence spectrum is measured and stored into the controller 103. For example, FIG. 7 shows a fluorescence spectrum in the case that the protective film 86 is formed on the ordinary pattern wafer with no bumps formed on the front side and the wavelength of the light to be applied to the protective film 86 is set to 385 nm. FIG. 8 shows a fluorescence spectrum in the case that the protective film 86 is formed on the bump wafer with bumps formed on the front side and the wavelength of the light to be applied to the protective film 86 is set to 385 nm. Further, FIG. 9 shows a fluorescence spectrum in the case that the protective film 86 is formed on the ordinary pattern wafer with no bumps formed on the front side and the light to be applied to the protective film 86 is LED light having a wavelength of 405 nm. FIG. 10 shows a fluorescence spectrum in the case that the protective film 86 is formed on the bump wafer with bumps formed on the front side and the light to be applied to the protective film 86 is LED light having a wavelength of 405 nm.

Figure 11:
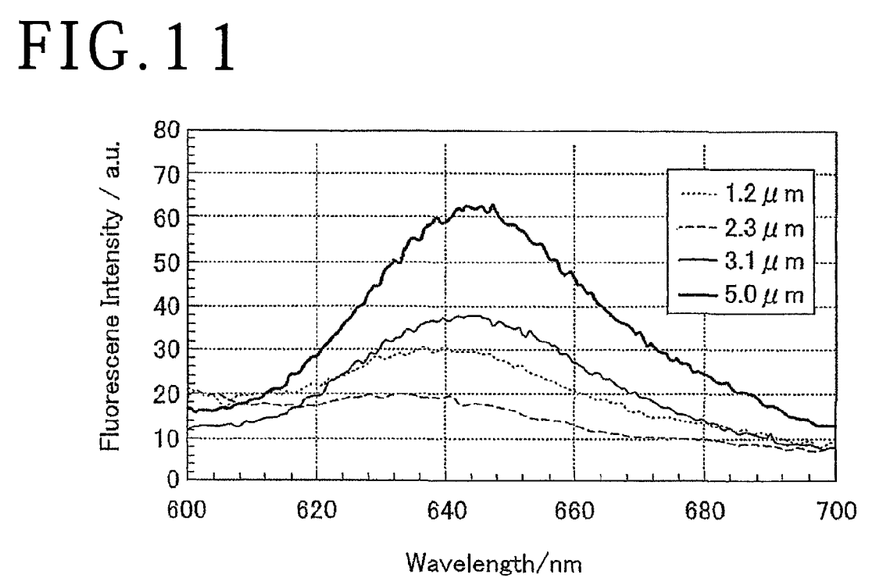
FIG. 11 is a graph showing a fluorescence spectrum in the case that light having a wavelength of 532 nm is applied to a bump wafer.
Figure 12:
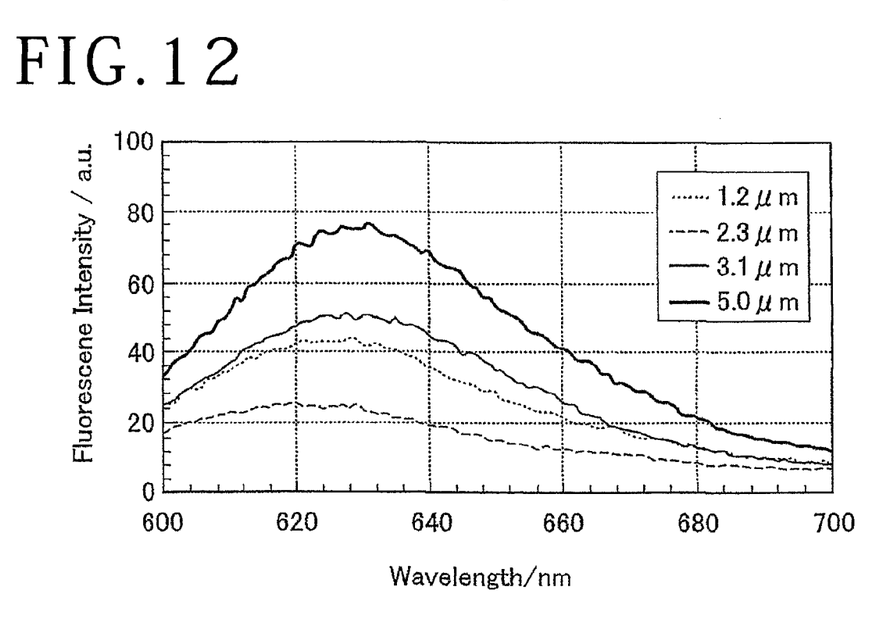
FIG. 12 is a graph showing a fluorescence spectrum in the case that light having a wavelength of 570 nm is applied to a bump wafer.

FIG. 11 shows a fluorescence spectrum in the case that the wavelength of the light to be applied to the protective film 86 is set to 532 nm. Also in the case that the wavelength of the light to be applied to the protective film 86 is different, the fluorescence spectrum is measured and stored into the controller 103. For example, FIG. 11 shows a fluorescence spectrum in the case that the protective film 86 is formed on the bump wafer with bumps formed on the front side and the wavelength of the light to be applied to the protective film 86 is set to 532 nm. FIG. 12 shows a fluorescence spectrum in the case that the protective film 86 is formed on the bump wafer with bumps formed on the front side and the wavelength of the light to be applied to the protective film 86 is set to 570 nm.

(1b) Threshold Deciding Step

Thereafter, the threshold of a predetermined fluorescence intensity corresponding to a predetermined thickness of the protective film 86 is determined according to the fluorescence spectra obtained above. That is, this step is a step of determining the threshold of the fluorescence intensity as the criterion for determination of whether or not the protective film 86 has a predetermined thickness. For example, as the threshold to be used as the criterion for determination of whether or not the thickness of the protective film 86 is sufficient, a peak value for the fluorescence intensity in each of the fluorescence spectra shown in FIGS. 5 to 10 is stored into the controller 103 shown in FIG. 3A. For example, in the case that the wavelength of the light to be applied to the protective film 86 is set to 365 nm, a peak value for the fluorescence intensity in the fluorescence spectrum shown in FIG. 5 is used as the threshold. More specifically, in the case that the thickness of the protective film 86 is 5.0 µm, the threshold is set to 350. In the case that the thickness of the protective film 86 is 3.1 µm, the threshold is set to 200. In the case that the thickness of the protective film 86 is 2.7 µm, the threshold is set to 110. In the case that the thickness of the protective film 86 is 2.3 µm, the threshold is set to 90. In the case that the thickness of the protective film 86 is 1.2 µm, the threshold is set to 70. When a protective film is actually formed on the workpiece W later and the intensity of the fluorescence emitted from the protective film by the application of ultraviolet light is not less than the threshold set above, it is determined that the thickness of the protective film is sufficient. As the threshold to be used as the criterion for determination, an integral value in a predetermined range may be used instead of the peak value for the fluorescence spectrum mentioned above. In this case, this integral value is compared with an integral value in the predetermined range in the fluorescence spectrum actually measured later.

(2) Spectrum Measuring Step

Thereafter, a protective film is formed on the front side Wa of the workpiece W to be laser-processed, and a fluorescence spectrum is measured for the protective film formed on the workpiece W, so as to determine whether or not the protective film has a predetermined thickness. Prior to forming the protective film, the back side Wb of the workpiece W is ground by using a grinding wheel or the like to reduce the thickness of the workpiece W to a predetermined thickness.

In this step, the protective film is formed on the front side Wa of the workpiece W in a manner similar to that in the reference spectrum making step mentioned above. Further, the fluorescence spectrum for the protective film formed on the workpiece W is measured in a manner similar to that in the reference spectrum making step mentioned above. The predetermined thickness of the protective film to be formed in this step is equal to the thickness of any one of the plural protective films formed in the reference spectrum making step mentioned above. In the case that the fluorescence spectra shown in FIGS. 5 to 10 are made, the thickness of the protective film to be actually formed on the workpiece W is set to any one of 1.2 µm, 2.3 µm, 2.7 µm, 3.1 µm, and 5.0 µm. In this step, every time the protective film is formed on the workpiece W by the protective film forming means 8 shown in FIG. 1, the workpiece W is next transferred to the position directly below the protective film detecting unit 10 to obtain a fluorescence spectrum for this workpiece W.

(3) Determining Step

Thereafter, the controller 103 shown in FIG. 3A, for example, compares the fluorescence spectrum (not shown) obtained in the above spectrum measuring step with the fluorescence spectrum obtained in the reference spectrum making step mentioned above and then determines whether or not the peak value for the fluorescence intensity measured in the spectrum measuring step is not less than the threshold decided in the threshold deciding step mentioned above.

For example, in the case that the workpiece with the protective film actually formed thereon is an ordinary pattern wafer with no bumps, that the wavelength of the LED light applied to the protective film in measuring the fluorescence spectrum is 365 nm, and that the desired thickness is 5.0 µm, it is determined that the thickness of the protective film is sufficient if the peak value for the fluorescence intensity obtained in the spectrum measuring step and shown in FIG. 5 is not less than 350. Conversely, if the peak value for the fluorescence intensity obtained in the spectrum measuring step is less than 350, it is determined that the thickness of the protective film is insufficient. In the case that the thickness of the protective film is insufficient, the workpiece W is returned to the holding table 80 of the protective film forming means 8 by operating the transfer mechanism 9 to form a protective film on this workpiece W again in the case that the protective film detecting unit 10 is not present in the same space as that of the protective film forming means 8 as in this preferred embodiment. In the case that the protective film detecting unit 10 is present in the same space as that of the protective film forming means 8 (e.g., in the case that the detecting unit 10 is located directly above the forming means 8), the transfer of the workpiece W to the chuck table 2 is not required, but the excitation light may be applied to the workpiece W held on the holding table 80. In forming a protective film again, the previous protective film may be first removed by cleaning and a new protective film may be next formed. Alternatively, a new protective film may be formed on the previous protective film. After forming the protective film again, the spectrum measuring step and the determining step are performed again.

In the case of detecting a portion having an insufficient thickness of the protective film formed on one workpiece, LED light is applied to the whole surface of the protective film and the fluorescence emitted from the whole surface of the protective film is detected by the photodetector 102 shown in FIG. 3C, for example. Thereafter, a fluorescence image obtained is binarized by the controller 103. For example, in the case that the fluorescence from the protective film is blue, the controller 103 compares RG and B in quantity of RGB constituting the image. For example, for each pixel composed of 8-bit information in the image, it is determined whether or not the following relation of Eq. (1) holds.

$$\{[R(0\text{-}255)+G(0\text{-}255)]/2+Q\}<\{B(0\text{-}255)\} \quad (1)$$

where 0-255 are pixel values and Q is an arbitrary value, which is decided according to the shape and condition of the workpiece, such as bumps.

When the above Eq. (1) holds, the image is made black in the controller 103, whereas when the above Eq. (1) does not hold, the image is made white in the controller 103. Then, either color is mapped on one screen to form a binary image. The controller 103 determines that a black part of this binary image corresponds to a portion of the protective film where the thickness is sufficient and that a white part of this binary image corresponds to a portion of the protective film where the thickness is insufficient. Thus, whether of not the protective film is formed is determined. Prior to forming the protective film, ultraviolet light may be applied to the front side of the workpiece W to thereby improve hydrophilicity and uniformly form the protective film.

(4) Laser Processing Step

After performing the determining step to determine that the thickness of the protective film 86 formed on the workpiece W is sufficient, the chuck table 2 holding the workpiece W is moved in the X direction and then positioned directly below the laser beam applying means 3. The workpiece W includes a silicon substrate and a dielectric film (one or more films of $SiO_2$, $SiN_x$, or polyimide) formed on the silicon substrate.

After detecting the division line L to be processed, the chuck table 2 is fed in the X direction and at the same time a laser beam is applied from the laser head 31 along this division line L, thereby performing ablation along this division line L. This laser processing is performed under the following conditions, for example.

Wavelength: 550 nm or less
Pulse width: 10 fs to 500 ns
Power: 0.1 to 100 W
Repetition frequency: 10 kHz to 1 GHz
Spot diameter: 2 to 70 μm
Feed speed: 100 to 5000 mm/second
Processing mode: single pulse or burst pulse
Beam shape: Gaussian type or top-hat type For example, in the case that the wavelength of the laser beam for processing the workpiece W is 355 nm, the laser processing is performed in plural passes along this division line L under the following conditions shown in Table 1.

TABLE 1

| | Pulse width [ns] | Power [W] | Repetition frequency [kHz] | Spot diameter [μm] | Feed speed [mm/s] | Index [mm] |
|---|---|---|---|---|---|---|
| First pass | 100 | 1.5 | 200 | 8 | 200 | 0.02 |
| Second pass | 100 | 1.5 | 200 | 8 | 200 | −0.02 |
| Third pass | 100 | 5.9 | 40 | 30 | 100 | 0.00 |
| Fourth pass | 100 | 5.9 | 40 | 30 | 100 | 0.00 |

In the first pass and the second pass, the laser processing is performed with low intensity to form two parallel grooves on the dielectric film, so as to prevent delamination (separation of the dielectric film). In the third pass, the laser processing is performed with high intensity to form a groove on the silicon substrate. That is, in the third pass, the groove is formed on the silicon substrate along this division line L so as to overlap the two parallel grooves formed in the first pass and the second pass. In the case that a low-permittivity insulator film (low-k film) or a passivation film is not formed on the front side of the workpiece (especially on each division line), the first pass and the second pass are not essential, but only the third and fourth passes may be performed. Further, the intensity of the laser beam in the first pass may be made lower than that of the laser beam in the second pass. Conversely, the intensity of the laser beam in the first pass may be made higher than that of the laser beam in the second pass. Further, the two parallel grooves to be formed in the first and second passes may be overlapped or separated. Further, any other various manners of laser processing may be adopted. That is, the manner of laser processing is not especially limited, but optimum processing conditions may be selected by adjusting variable laser parameters according to the material to be processed. Further, light emitted from a light source for laser processing may be branched into two or more laser beams. In the case of two laser beams, they may be used in simultaneously performing the first pass and the second pass. In the case of three or more laser beams, they may be applied in different directions parallel, perpendicular, and oblique to the processing direction. The spacing between these branched beams is preferably made sufficient to relax a thermal effect.

In the case that the pulse width is subnano second, the beam spots are preferably overlapped at a high rate of 50% or more, so as to prevent the delamination. To prevent the delamination and achieve high-speed processing, a laser oscillator having a high repetition frequency of MHz or more is used. Further, in the case of high-speed processing, a polygon mirror may be used to apply a laser beam along the division line linearly or nonlinearly. Also in the case that the pulse width is subnano second, various manners of laser processing may be adopted as in the nano-second laser processing mentioned above. That is, also in this case, optimum processing conditions may be selected by adjusting variable laser parameters according to the material to be processed.

The groove to be formed in this laser processing preferably has a shape such that the lateral center of the groove is deeper than the other portion. In performing the laser processing, an assist gas such as oxygen, nitrogen, argon, and helium may be discharged to remove a substance melted and evaporated. Alternatively, such a substance may be sucked by using a suction nozzle or the like.

After performing the laser processing (ablation) along the above predetermined division line L, the indexing means 5 is operated to move the chuck table 2 in the Y direction and then similarly perform the laser processing along the next division line L. After performing the laser processing along all of the other division lines L extending in a first direction, the chuck table 2 is rotated 90 degrees to similarly perform the laser processing along all of the other division lines L extending in a second direction perpendicular to the first direction. In this manner, a plurality of laser processed grooves are formed along all of the division lines L.

Debris generated and scattered by the ablation adheres to the upper surface of the protective film 86. In the determining step mentioned above, it is determined that the protective film 86 formed on the workpiece W to be laser-processed has a sufficient thickness. Accordingly, it is possible to prevent that the debris may adhere to the devices D.

Although the protective film 86 is formed on the whole surface of the front side Wa of a workpiece W having high bumps, the debris of silicon may react with oxygen in the air to produce a residue such as silicon oxide ($SiO_x$), which cannot be removed by cleaning with water, and this residue may adhere to the surface of each bump and it is difficult to remove. In this case, isotropic plasma etching is performed to remove the residue adhering to the surface of each bump.

Further, metal oxide such as $TiO_2$ may be mixed in the water-soluble liquid resin 810 for forming the protective film 86, so as to promote the laser processing. Further, in the case that silica ($SiO_2$) is mixed in the water-soluble liquid resin 810, delamination can be suppressed owing to the low expansion coefficient and high thermal diffusivity of silica. The metal oxide to be mixed has a particle size of 10 to 200 nm, and it is mixed in an amount of about 0.01 to 10 parts by weight per 100 parts by weight of water-soluble resin. The shape of the particles of the metal oxide may be circular or elongated like a needle.

In this manner, the spectrum measuring step, the determining step, and the laser processing step are repeated for all of the workpieces W stored in the cassette 60 shown in FIG. 1. As a result, it is possible to obtain the devices with no debris from each workpiece W.

After dividing each workpiece W along the division lines L to obtain the individual devices attached to the tape T, the individual devices attached to the tape T are transferred from the chuck table 2 to the protective film forming means 8 by operating the transfer mechanism 9. In the protective film forming means 8, a cleaning water is discharged from the cleaning liquid nozzle 82 toward the protective film 86 formed on the workpiece W held on the holding table 80, thereby removing the protective film 86 formed on the front side of each device.

While the laser processing apparatus 1 has a function of forming a protective film on the front side Wa of the workpiece W, a function of determining whether or not the protective film formed has a desired thickness, and a function of laser-processing the workpiece W in the above preferred embodiment, these functions may be separately performed by individual apparatuses. Further, while the unit for measuring a fluorescence spectrum and the unit for forming a protective film are provided adjacent to each other in the same space in this preferred embodiment, these units may be provided in different spaces.

The fluorescence spectra shown in FIGS. 5 to 10 show the measurement results in the case that Hogomax as a water-soluble resin provided by DISCO Corporation is used as the water-soluble liquid resin 810 shown in FIG. 4A and the water-soluble liquid resin 810 contains an absorbing agent (ferulic acid) capable of absorbing a pulsed laser beam having a wavelength of 355 nm (the water-soluble liquid resin 810 showing no color to pale yellow color in appearance). This water-soluble liquid resin 810 is formed on the front side of each wafer. The fluorescence spectra shown in FIGS. 11 and 12 show the measurement results in the case that the absorbing agent contained in Hogomax is changed to an absorbing agent (blue coloring matter) capable of absorbing a pulsed laser beam having a wavelength of 532 nm (this water-soluble liquid resin 810 showing red to blue color in appearance).

More specifically, the fluorescence spectra shown in FIGS. 5 and 6 are those in the case that the wavelength of excitation light to be applied to the protective film is 365 nm. As apparent from FIGS. 5 and 6, there is a correlation between the thickness of the protective film and the fluorescence intensity. Accordingly, these fluorescence spectra can be used for the determination of whether or not the protective film has a desired thickness.

The fluorescence spectrum shown in FIG. 7 is that in the case that the wavelength of the excitation light is 385 nm and the protective film is formed on a pattern wafer. As apparent from FIG. 7, the fluorescence intensity increases with an increase in thickness of the protective film. Accordingly, in determining the thickness of an actual protective film formed on a pattern wafer, it is possible to determine whether or not the actual protective film has a predetermined thickness by comparing the fluorescence spectra according to the thickness.

The fluorescence spectrum shown in FIG. 8 is that in the case that the wavelength of the excitation light is 385 nm and the protective film is formed on a bump wafer. As apparent from FIG. 8, there is no correlation between the thickness of the protective film and the fluorescence intensity in the case that the protective film is thin. However, in the case that the protective film is thick (5.0 μm or 3.1 μm), there is a correlation between the thickness of the protective film and the fluorescence intensity. Accordingly, in the case that the actual protective film is thick (e.g., 3.1 μm or more), it is possible to determine whether or not the thickness of the actual protective film has a predetermined thickness by comparing the fluorescence spectra according to the thickness.

The fluorescence spectra shown in FIGS. 9 and 10 are those in the case that the wavelength of the excitation light is 405 nm. As apparent from FIGS. 9 and 10, there is no correlation between the thickness of the protective film and the fluorescence intensity. Accordingly, these fluorescence spectra are not used for the determination of the thickness of the protective film.

The fluorescence spectra shown in FIGS. 11 and 12 are those in the case that the wavelength of the excitation light is set to 532 nm and 570 nm, respectively, and the protective film is formed on a bump wafer. As apparent from FIGS. 11 and 12, the fluorescence intensity increases with an increase in thickness of the protective film. Accordingly, in determining the thickness of an actual protective film on a bump wafer, it is possible to determine whether or not the actual protective film has a predetermined thickness by comparing the fluorescence spectra according to the thickness.

Figure 13A:
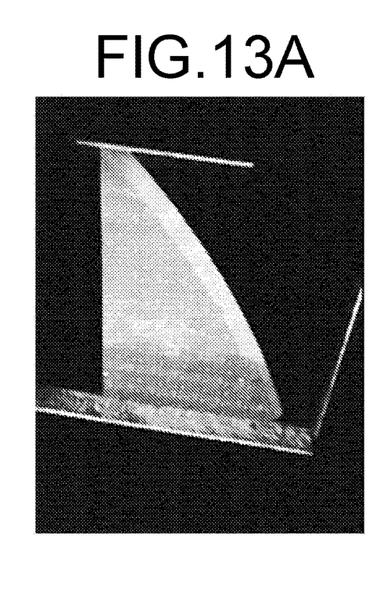
FIG. 13A is a photograph in the case that light having a wavelength of 365 nm is applied to a bump wafer having a protective film containing an absorbing agent capable of absorbing a laser beam.
Figure 13B:
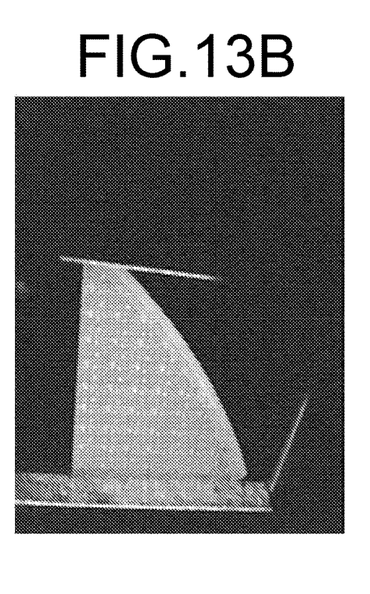
FIG. 13B is a photograph similar to FIG. 13A, showing the case that the protective film does not contain the absorbing agent.
Figure 13C:
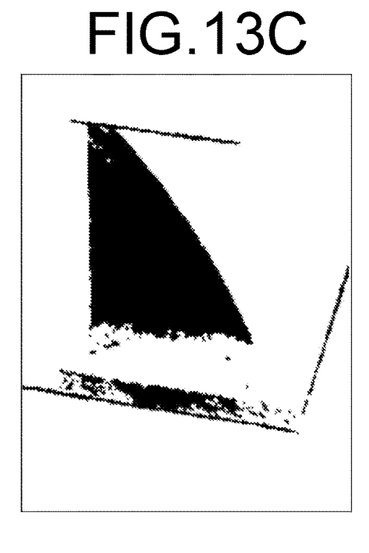
FIG. 13C is a binary image of the photograph shown in FIG. 13A.
Figure 13D:
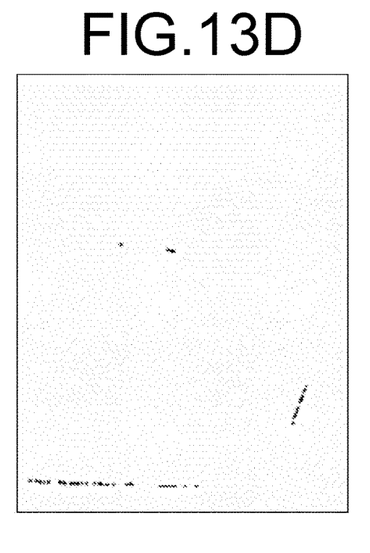
FIG. 13D is a binary image of the photograph shown in FIG. 13B.
Figure 14A:
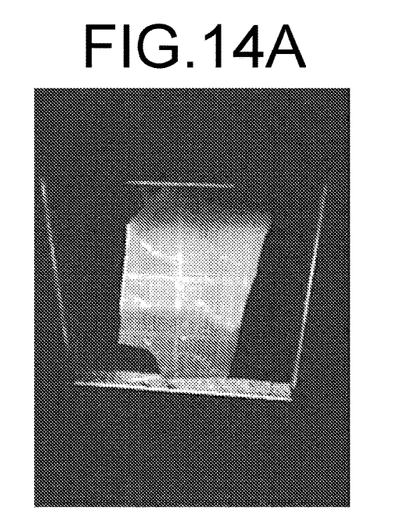
FIG. 14A is a photograph in the case that light having a wavelength of 365 nm is applied to a pattern wafer having a protective film containing an absorbing agent capable of absorbing a laser beam.
Figure 14B:
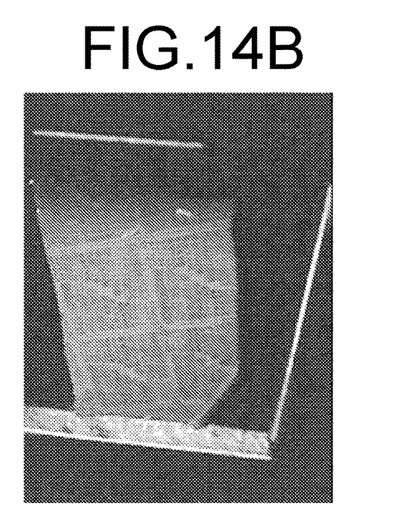
FIG. 14B is a photograph similar to FIG. 14A, showing the case that the protective film does not contain the absorbing agent.
Figure 14C:
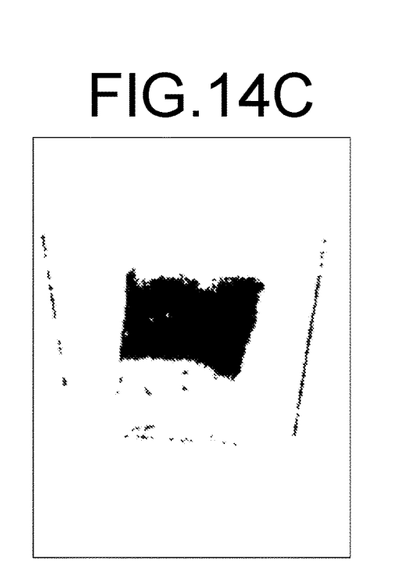
FIG. 14C is a binary image of the photograph shown in FIG. 14A.
Figure 14D:
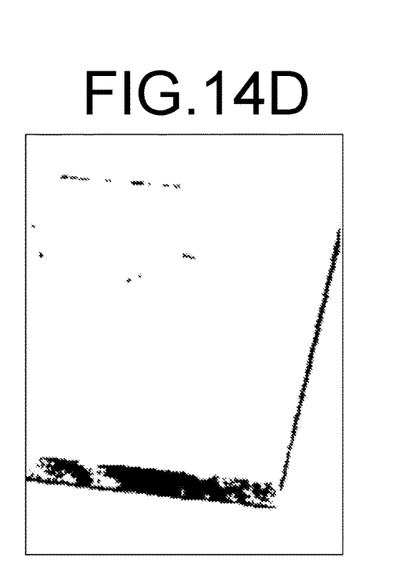
FIG. 14D is a binary image of the photograph shown in FIG. 14B.

FIGS. 13A and 13B are real images (photographs) and FIGS. 13C and 13D are binary images respectively corresponding to FIGS. 13A and 13B in the case of a bump wafer. On the other hand, FIGS. 14A and 14B are real images (photographs) and FIGS. 14C and 14D are binary images respectively corresponding to FIGS. 14A and 14B in the case of a pattern wafer. FIG. 13A is the real image in the case that the protective film contains the absorbing agent, and FIG. 13B is the real image in the case that the protective film does not contain the absorbing agent. Similarly, FIG. 14A is the real image in the case that the protective film contains the absorbing agent, and FIG. 14B is the real image in the case that the protective film does not contain the absorbing agent. FIGS. 13A to 14D are shown to verify the effectiveness of the present invention by the comparison between the case that the absorbing agent is present in the protective film and the case that the absorbing agent is absent in the protective film. In the case that the protective film containing the absorbing agent is formed on the bump wafer, blue fluorescence is emitted from an area where the protective film is formed by applying LED light having a wavelength of 365±10 nm. As shown in FIG. 13A, this blue fluorescence is shown as a pale white area. On the other hand, in the case that the protective film not containing the absorbing agent is formed on the bump wafer, the blue fluorescence is not emitted and no white area is shown in FIG. 13B.

Similarly, in the case that the protective film containing the absorbing agent is formed on the pattern wafer, blue fluorescence is emitted from an area where the protective film is formed by applying LED light having a wavelength of 365±10 nm. As shown in FIG. 14A, this blue fluorescence is shown as a pale white area. On the other hand, in the case that the protective film not containing the absorbing agent is formed on the pattern wafer, the blue fluorescence is not emitted and no white area is shown in FIG. 14B.

The real images obtained above were subjected to binary image analysis by Eq. (1) mentioned above. By adjusting the arbitrary value Q in Eq. (1), the protective film containing the absorbing agent was displayed in black as shown in FIGS. 13C and 14C, whereas the protective film not containing the absorbing agent was displayed in white as shown in FIGS. 13D and 14D. In this manner, the present invention is a measuring method derived from the fluorescence due to the absorbing agent contained in the protective film.

In FIGS. 13A and 14A, the formed area of the protective film was artificially prepared. This formed area is a lower area on each wafer. As shown in FIGS. 13A and 14A, no fluorescence was seen in this formed area. Further, as shown in FIGS. 13C and 14C, this formed area was displayed in white as a binary image. In this manner, by measuring the fluorescence due to the absorbing agent contained in the protective film, it is possible to determine whether or not the protective film is present.

In this preferred embodiment, the continuous-wave light having a single wavelength used for measurement of the fluorescence intensity in an ultraviolet region includes light having a wavelength of 365 nm and light having a wavelength of 385 nm. In the case of using the light having a wavelength of 365 nm, there is a definite correlation between the thickness of the protective film and the fluorescence intensity. That is, a large optical absorption coefficient can be obtained, so that the fluorescence intensity due to the absorbing agent can be increased. Accordingly, it can be easily determined whether or not the protective film is present. Further, in the fluorescence spectra shown in FIGS. 5 to 8 which can be used for the determination of the thickness of the protective film, it is apparent that the peak wavelength as a reference for setting of the threshold is longer than the wavelength of the excitation light and falls within the range of 400 to 500 nm.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. A protective film detecting method of detecting the formed condition of a protective film formed on a front side of a workpiece, so as to protect the front side of said workpiece from processing dust generated in laser-processing said workpiece by applying a pulsed laser beam having a wavelength in an ultraviolet region or visible region to said workpiece, said protective film being formed of a water-soluble resin containing an absorbing agent capable of absorbing said pulsed laser beam, said protective film detecting method comprising:
    a fluorescence intensity measuring step of forming a plurality of reference protective films having different thicknesses on the front sides of a plurality of reference workpieces, next applying excitation light absorbable by said absorbing agent to said reference protective films, and next measuring the intensity of fluorescence emitted from said absorbing agent contained in each reference protective film due to the absorption of said excitation light;
    a threshold deciding step of deciding a threshold of the fluorescence intensity corresponding to a desired one of said different thicknesses of said reference protective films according to the fluorescence intensity measured in said fluorescence intensity measuring step; and
    a determining step of applying said excitation light to said protective film formed on the front side of said workpiece, next measuring the intensity of fluorescence emitted from said absorbing agent contained in said protective film due to the absorption of said excitation light, next comparing the fluorescence intensity from said absorbing agent contained in said protective film with said threshold decided in said threshold deciding step, and next determining whether or not said protective film has said desired thickness.

2. The protective film detecting method according to claim 1, wherein the wavelength of said pulsed laser beam is 355 nm;
    the wavelength of said excitation light is in the range of 355 to 400 nm; and
    the peak wavelength of said fluorescence at which the fluorescence intensity becomes a peak value is longer than the wavelength of said excitation light and falls within the range of 365 to 600 nm.

3. The protective film detecting method according to claim 1, wherein the wavelength of said pulsed laser beam is 532 nm;
    the wavelength of said excitation light is in the range of 480 to 600 nm; and
    the peak wavelength of said fluorescence at which the fluorescence intensity becomes a peak value is longer than the wavelength of said excitation light and falls within the range of 570 to 700 nm.

* * * * *